United States Patent [19]
Cordi et al.

[11] Patent Number: 5,536,719
[45] Date of Patent: Jul. 16, 1996

[54] BENZOTHIADIAZINE COMPOUND

[75] Inventors: Alex Cordi, Suresnes; Michael Spedding, Le Vesinet; Bernard Serkiz, Servon Brie Comte Robert; Jean Lepagnol, Chaudon; Patrice Desos, Courbevoie; Philippe Morain, Issy les Moulineaux, all of France

[73] Assignee: Adir et Compagnie, Courbevoie, France

[21] Appl. No.: 500,609

[22] Filed: Jul. 11, 1995

[30] Foreign Application Priority Data

Jul. 12, 1994 [FR] France ................. 94 08603

[51] Int. Cl.⁶ ............ C07D 513/04; A61K 31/54
[52] U.S. Cl. ............. 514/222.8; 544/9
[58] Field of Search .............. 544/9; 514/222.8

[56] References Cited

PUBLICATIONS

Cameroni et al, Chemical Abstracts, vol. 90, entry 33765 (1979).
Bernabei et al, Chemical Abstracts, vol. 85, entry 143068 (1976).
Cameroni et al, Chemical Abstracts, vol. 77, entry 126583 (1972).

Primary Examiner—John M. Ford
Attorney, Agent, or Firm—Gordon W. Hueschen

[57] ABSTRACT

A compound of formula (I):

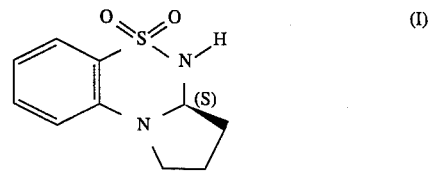

in the form of its S enantiomer, its addition salts with a pharmaceutically acceptable acid or base and medicinal product containing the same are useful for the treatment or prevention of pathologies associated with dysfunction of glutamatergic neurotransmission.

3 Claims, No Drawings

BENZOTHIADIAZINE COMPOUND

BACKGROUND OF THE INVENTION

The present invention relates to a new benzothiadiazine compound.

1. Field of the Invention

It is now acknowledged that excitatory amino acids, and most particularly glutamate, play a crucial role in the physiological processes of neuronal plasticity and in the mechanisms underlying learning and memory. Recently, pathophysiological studies have indicated clearly that a deficit in glutamatergic neurotransmission is closely associated with the development of Alzheimer's disease (Neuroscience and Biobehavioral reviews, 1992, 16, 13–24; Progress in Neurobiology, 1992, 39, 517–545).

Moreover, numerous works have illustrated in recent years the existence of receptor subtypes for excitatory amino acids and of their functional interactions (Molecular Neuropharmacology, 1992, 2, 15–31).

Among these receptors, the AMPA receptor ("a-amino-3-hydroxy-5-methyl-4-isoxazolepropionic acid") appears to be the one most involved in physiological neuronal excitability phenonema and especially in those involved in the processes of memorization. For example, learning has been shown to be associated with the increase in the binding of AMPA to its receptor in the hippocampus, one of the regions of the brain essential for mnemocognitive processes. Similarly, nootropic agents such as aniracetam have been described very recently as positively modulating the AMPA receptors of neuronal cells (Journal of Neurochemistry, 1992, 58, 1199–1204).

2. Description of the Prior Art

Very recently, compounds of benzamide structure have been described as possessing the same mechanism of action and as improving memory performance (Synapse, 1993, 15, 326–329). The compound BA 74, in particular, is the most active among these novel pharmacological agents.

DETAILED DESCRIPTION OF THE INVENTION

More specifically, the present invention relates to the S isomer of 5,5-dioxo-2,3,3a,4-tetrahydro-1H-pyrrolo[2,1-c][1,2,4]b enzothiadiazine of formula (I):

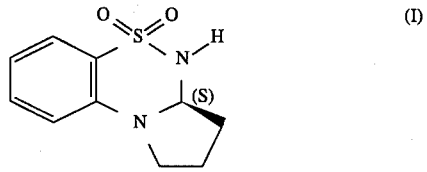

as well as its addition salts with a pharmaceutically acceptable acid or base.

This compound, in racemic form, has been described in the literature by M. T. Bernabei et al. (Il Farmaco, Ed. Sc., 1976, 31, issue 7, 508–516).

This compound, in racemic form, is furthermore known as having hypotensive and bradycardiac activities as shown by R. Cameroni et al. (Il Farmaco, Ed. Sc., 1978, vol. 33, issue 9, 713–720).

The Applicant has now discovered that the S isomer of this compound was not only novel but possessed, surprisingly, powerful facilitative activity on the AMPA current, thereby making it useful in the treatment of diseases involving the AMPA receptor.

Hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric, oxalic and similar acids may be mentioned among the pharmaceutically acceptable acids, no limitation being implied.

Sodium hydroxide, potassium hydroxide, sodium bicarbonate and the like may be mentioned among the pharmaceutically acceptable bases, no limitation being implied.

The present invention also relates to the process for obtaining this isomer, wherein the compound of formula (II):

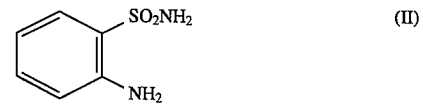

is reacted with the acid chloride of formula (III) in the presence of triethylamine, in tetrahydrofuran medium:

to give the compound of formula (IV):

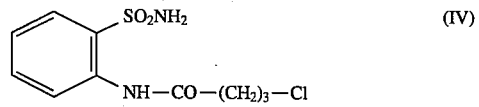

which is then cyclized in basic medium, to give the compound of formula (V):

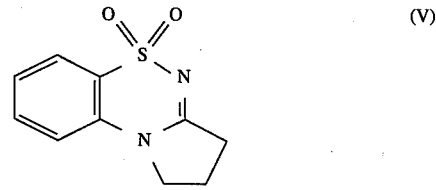

which compound of formula (V) undergoes:
either a reduction, in alcoholic medium, in the presence of sodium borohydride, to give the compound of formula (VI), in racemic form,

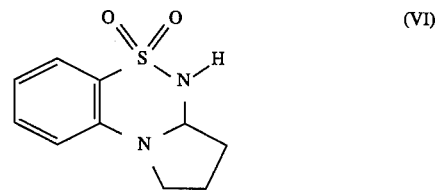

the isomers of which are separated by chiral-phase liquid chromatography, to give the enantiomerically pure S isomer of formula (I), or a stereospecific reduction in the presence of hydrogen using a metal catalyst derived from ruthenium, rhodium, palladium, platinum or iridium complexed with a chiral ligand such as 2,2'-bis(diphenylphosphino)-1,1'-binaphthyl or BINAP, or, in the presence of borane or aluminum hydride which has been reacted beforehand with chiral ligand such as 4-dimethylamino-1,2-diphenyl-3-methyl-2-butanol, leading directly to the enantiomerically pure S isomer of formula (I), which compound of formula (I) is purified, if so desired, by a standard purification technique and which is converted, if appropriate, into its addition salts with a pharmaceutically acceptable acid or base.

The compound of formula (I) may also be obtained by stereospecific synthesis using a chiral auxiliary such as a-methylbenzylamine which is reacted with 2-aminobenzenesulfonyl chloride. The aminosulfonamide formed is reacted with 4-chlorobutanoyl chloride, reduced, cyclized and epimerized by successive treatment with a reducing agent such as sodium borohydride and then with a base such as sodium hydroxide. The diastereoisomer formed is then optionally purified and the chiral auxiliary is removed by hydrogenolysis in the presence of a metal catalyst.

The compound of the present invention has advantageous pharmacological properties since it may selectively potentiate the excitatory electrophysiological phenomena induced by AMPA, either in Xenopus oocytes expressing glutamate receptors by injection of mRNA from rat cortex, or in the hippocampus during the electrical stimulation of the glutamatergic neurotransmission pathways.

As may be seen from the electrophysiological studies carried out with regard to the excitability induced by AMPA expressed in Xenopus oocytes or naturally present in the hippocampus, these effects are always greater than those of the compounds taken as reference and impart pharmacological and therapeutic potentialities to the compound of the invention with regard to disorders induced by dysfunction of glutamatergic neurotransmission and especially those associated with the AMPA receptor.

Glutamatergic neurotransmission has now been widely demonstrated as being crucial for the physiological processes of learning and of the memory, and more widely for processes governing the faculties of attention, concentration and vigilance. More particularly, the receptor subtype referred to as AMPA appears to play a fundamental role in these processes.

The compound of the present invention has shown advantageous pharmacological effects since it can selectively facilitate activation of this AMPA receptor. These effects are, surprisingly, much more intense than those of the reference compounds previously described (Diazoxide and Aniracetam) or recently proposed (BA 74), or indeed those observed with the racemic mixture.

The compound of the invention is thus useful as an agent for facilitating the activation induced by glutamic acid in the AMPA receptors and thus constitutes a therapeutic agent for the treatment and prevention of pathologies associated with dysfunction of glutamatergic neurotransmission such as:
memocognitive disorders associated with age and depressive or anxiety syndromes,
memory deficiencies of progressive neurodegenerative diseases such as, for example, Alzheimer's disease, Pick's disease, Huntington's chorea and schizophrenia,
sequels to acute neurodegenerative diseases such as, for example, ischemia and epilepsy.

Another subject of the present invention is pharmaceutical compositions containing the compound of formula (I), in combination with one or more pharmaceutically acceptable excipients or vehicles.

Among the pharmaceutical compositions according to the invention there may be mentioned, by way of example and in a non-limiting manner, those which are suitable for oral, rectal, nasal or parenteral administration and especially tablets, coated tablets, gelatin capsules, packets, sachets, granules, pills, suppositories, aerosols, wafer capsules and injectable or drinkable solutions.

The dosage varies from one individual to the next, depending on the age, weight and sex of the patient, the administration route chosen, and the nature and intensity of the complaint. The doses used range between 1 and 500 mg for a treatment, which may be divided into 1 to 3 doses taken per 24 h.

The examples which follow illustrate the invention and do not limit it in any way.

EXAMPLE 1

(3aS)-5,5-Dioxo-2,3,3a,4-tetrahydro-1H-pyrrolo[2,1-c][1,2,4]benzothiadiazine

Stage A: 5,5-Dioxo-2,3-dihydro-1H-pyrrolo[2,1-c][1,2,4]-benzothi adiazine 5.8 mmol of 2-aminobenzenesulfonamide are dissolved in tetrahydrofuran (THF) at room temperature. This solution is cooled on an ice bath, and 6 mmol of 4-chlorobutanoyl chloride and 6 mmol of triethylamine are successively added. The mixture is stirred for 16 hours at room temperature, filtered and evaporated. The yellow solid obtained is taken up in 40 ml of 1N sodium hydroxide and stirred at room temperature. After complete dissolution, a white precipitate appears; it is filtered off and gives the expected product after crystallization from an ethanol/water (4/1) mixture.

Stage B: 5,5-Dioxo-2,3,3a,4-tetrahydro-1H-pyrrolo[2,1-c]-[1,2,4]benzothiadiazine The compound obtained in the above stage is dissolved in 30 ml of ethanol. 26 mmol of sodium hydride are added to the solution, which is stirred for 90 minutes and evaporated. The residue thus obtained is taken up in water and extracted with dichloromethane. After drying and evaporation of the organic phases, the expected product is obtained, which is crystallized from ethyl acetate.
Melting point: 202° C.

|  | Elemental microanalysis: | | | |
| --- | --- | --- | --- | --- |
|  | C % | H % | N % | S % |
| calculated | 53.55 | 5.39 | 12.49 | 14.30 |
| found | 53.98 | 5.40 | 12.38 | 14.23 |

Stage C: (3aS)-5,5-Dioxo-2,3,3a,4-tetrahydro-1H-pyrrolo-[2,1-c][1,2,4]benzothiadiazine The enantiomers of the compound obtained in the above stage are separated by preparative chiral liquid chromatography on a Chiralpak AS column (50×2 cm). The elution is performed using a heptane/ethanol (½) mixture as solvent, at a speed of 1.5 ml/min. The separation is performed with samples containing 80 mg of the racemic mixture in 2.5 ml of acetone. The fractions corresponding to each elution peak are combined and evaporated. The R isomer is eluted first, the active S isomer is eluted second. The enantiomeric purity of each isomer is then checked by analytical chiral HPLC chroma-tography under the same conditions as those used for the preparative separation. The enantiomers obtained are recrystallized from ethyl acetate. The absolute con-figuration of the active (S) enantiomer was determined on a monocrystal of the product by X-ray diffraction.

S Isomer:

Melting point: 218° C.

| Elemental microanalysis: | | | | |
|---|---|---|---|---|
| | C % | H % | N % | S % |
| calculated | 53.55 | 5.40 | 12.49 | 14.30 |
| found | 53.80 | 5.44 | 12.02 | 14.05 |

R Isomer:

Melting point: 219° C.

| Elemental microanalysis: | | | | |
|---|---|---|---|---|
| | C % | H % | N % | S % |
| calculated | 53.55 | 5.40 | 12.49 | 14.30 |
| found | 53.80 | 5.57 | 12.63 | 14.26 |

Pharmacological study of the compound of the invention

Example 2:

Study of the excitatory currents induced by AMPA in Xenopus oocytes a—Method:

mRNAs are prepared from male Wistar rat cerebral cortex by the guanidium thiocyanate/phenol/chloroform method. The poly($A^+$) mRNAs are isolated by chromatography on oligo-dT cellulose and injected at an amount of 50 ng per oocyte. The oocytes are left to incubate for 2 to 3 days at 18° C. in order to allow expression of the receptors, and are then stored at 8°–10° C.

The electrophysiological recording is performed in a plexiglass® chamber at 20°–24° C. in OR2 medium (J. Exp. Zool., 1973, 184, 321–334) by the "voltage-clamp" method with 2 electrodes, a 3rd electrode placed in the bath serving as reference.

All the compounds are applied via the incubation medium and the electric current is measured at the end of the period of application. The AMPA is used at a concentration of 30 mM. The concentration which doubles (EC2X) or which increases five-fold (EC5X) the intensity of the current induced by AMPA alone (50 to 100 nA) is determined for each compound studied.

b—Results:

The compound of the invention very strongly potentiates the excitatory effects of AMPA and its activity is considerably greater than those of the reference compounds as well as those of the racemic mixture or of the R isomer as indicated in the following table:

| Compound | EC2X (µM) | EC5X (µM) |
|---|---|---|
| Example 1 (S isomer) | 35 | 70 |
| Racemic mixture | 60 | 160 |
| R isomer | 300 | >1000 |
| BA 74 | 45 | 110 |
| Diazoxide | 400 | 1000 |
| Aniracetam | 1300 | 5000 |

Furthermore, this facilitative activity of the compound of the invention is selective for the AMPA receptor since no potentiation of the current is observed when the glutamatergic agonist used is NMDA or kainate (KA).

| | AMPA | KA | NMDA |
|---|---|---|---|
| EC2X (µM) S isomer | 35 | >300 | >>300 |

EXAMPLE 3

Study of the synaptic excitatory potentials induced by electrical stimulation on a slice of hippocampus a—Method:

Transverse slices of hippocampus (500 mM) from a male Wistar rat are prepared using a "tissue chopper" and then incubated for 45 minutes in calcium-free medium containing 10 mM $Mg^{++}$. They are then stabilized in Krebs adjusted to pH 7.35 and oxygenated with $O_2/CO_2$ (95%/5%) at room temperature.

The slices are submerged at 35° C. and the excitatory postsynaptic potentials (EPSP) are recorded in the dendritic field of the granulocytes of the dentate gyms during stimulation (50–100 mA, 50 msec) every 30 seconds of the perforating route via a tungsten bipolar electrode.

The EPSPs are acquired and analyzed by means of an A–D converter, a TL-1 interface and "pCLAMP" software.

The amplitude and duration of the EPSPs are evaluated on the negative wave relative to the base current.

The compounds are applied for 10 to 20 minutes in the superfusion bath containing $MgSO_4$ (1 mM) in order to block the activation of the NMDA receptors. The concentration increasing the amplitude of the EPSP by 50% (A50) is determined for each compound.

b—Results:

The compound of the invention increases the amplitude of the EPSP at lower doses than the reference compounds, the racemic mixture or the R isomer, as shown by the following table:

| Compound | A50 (mM) |
|---|---|
| Example 1 (S isomer) | 90 |
| Racemic mixture | >300 |
| R isomer | >>1000 |
| BA 74 | >300 |
| Diazoxide | 560 |
| Aniracetam | 3000 |

We claim:

1. A compound selected from those of formula (I):

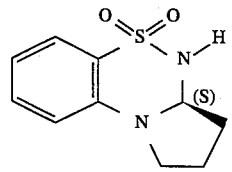

in the form of its S enantiomer essentially free of its R enantiomer and its addition salts with a pharmaceutically-acceptable acid or base.

2. A method for treating an animal living body afflicted with a condition requiring the treatment or prevention of pathologies associated with dysfunction of glutamatergic neurotransmission, comprising the step of administering to the living body an amount of a compound of claim 1 which is effective for alleviation of said condition.

3. A pharmaceutical composition useful in the treatment or prevention of a pathology associated with dysfunction of glutamatergic neurotransmission, comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,536,719
DATED : July 16, 1996
INVENTOR(S) : Cordi et al.

It is certified that error appears in the above-indentified patent and that said Letters Patent is hereby corrected as shown below:

Column 1, line 44:  Delete "[" at end of the line.

Column 1, line 45:  Insert -- [ -- at beginning of the line.

Signed and Sealed this

First Day of October, 1996

Attest:

BRUCE LEHMAN

Attesting Officer     Commissioner of Patents and Trademarks